(12) United States Patent
Gerhard et al.

(10) Patent No.: US 7,354,589 B2
(45) Date of Patent: Apr. 8, 2008

(54) MULTIPLE ANTIGENIC AGENTS AND METHODS FOR USING THE SAME

(75) Inventors: Walter Gerhard, Philadelphia, PA (US); Laszlo Otvos, Jr., Audubon, PA (US)

(73) Assignee: The Wistar Institute, Philadelphia, PA (US)

( * ) Notice: Subject to any disclaimer, the term of this patent is extended or adjusted under 35 U.S.C. 154(b) by 0 days.

(21) Appl. No.: 11/093,107

(22) Filed: Mar. 29, 2005

(65) Prior Publication Data

US 2008/0050397 A1 Feb. 28, 2008

Related U.S. Application Data

(63) Continuation-in-part of application No. 10/757,692, filed on Jan. 14, 2004, now abandoned.

(60) Provisional application No. 60/441,374, filed on Jan. 16, 2003.

(51) Int. Cl.
*A61K 39/385* (2006.01)
*C07K 17/00* (2006.01)

(52) U.S. Cl. .................. 424/193.1; 530/403

(58) Field of Classification Search ............ 424/209.1, 424/185.1, 184.1; 514/12; 530/387.3, 322, 530/324
See application file for complete search history.

(56) References Cited

FOREIGN PATENT DOCUMENTS

WO WO 9738011 A1 * 10/1997

OTHER PUBLICATIONS

Tamura et al., "Acceleration of Influenza Virus Clearance by Th1 Cells in the Nasal Site of Mice Immunized Intranasally with Adjuvant-Combined Recombinant Nucleoprotein," The Journal of Immunology, 156, pp. 3892-3900 (1996).*

See Enclosed Results 18 of 21, Structure search in HCAPLUS (2007).*
Falgui et al., "Rationally designed strings of promiscuous CD4+ T cell epitopes provide help to *Haemophilus influenzae* type b oligosaccharide:a model for new conjugate vaccines", Eur. J. Immunol. 2001 31:3816-3824.
Fiers et al., "Soluble recombinant influenza vaccines", Phil. Trans. R. Soc. Lond. B 2001 356:1961-1963.
Gerhard et al., "Identification of Eight Determinants in the Hemagglutinin Molecule of Influenza Virus A/PR/8/34 (H1N1) Which Are Recognized by Class II-Restricted T Cells from BALB/c Mice", J. Virology 1991 65(1) :364-372.
Heinen et al., "Vaccination of pigs with a DNA construct expressing an influenza virus M2-nucleoprotein fusion protein exacerbates disease after challenge with influenza A virus", J. General Virology 2002 83:1851-1859.
Neirynck et al., "A universal influenza A vaccine based on the extracellular domain of the M2 protein", Nature Medicine 1999 5(10) :1157-1163.
Zaliauskiene et al., "Enhancement of MHC Class II- Restricted Responses by Receptor-Mediated Uptake of Peptide Antigens[1]", J. Immunol 2002 169:2337-2345.
Kragol et al., "Synthesis of a Disulfide-Linked Octameric Peptide Construct carrying Three Different Antigenic Determinants", Bioorganic & Medicinal Chemistry Letters 2001 11:1417-1420.
Kragol et al., "Orthogonal solid-phase synthesis of tetramannosylated peptide constructs carrying three independent branched epitopes", Tetrahedron 2001 57:957-966.
Mozdzanowska et al., "Induction of influenza type A virus-specific resistance by immunization of mice with a synthetic multiple antigenic peptide vaccine that contains ectodomains of matrix protein 2", Vaccine 2003 21:2616-2626.

* cited by examiner

*Primary Examiner*—Mary E. Mosher
(74) *Attorney, Agent, or Firm*—Licata & Tyrrell PC (57) ABSTRACT

The present invention provides multiple antigenic agents compositions and the use thereof to prevent or treat viral infections. The multiple antigenic agents of the invention contain at least one of a B cell determinant, a T cell determinant, or a targeting molecule attached to a core peptide composed of Lys-Gly repeats.

5 Claims, 1 Drawing Sheet

SEQUENCE LISTING

<160> NUMBER OF SEQ ID NOS: 14

<210> SEQ ID NO 1
<211> LENGTH: 5

```
<212> TYPE: PRT
<213> ORGANISM: Artificial Sequence
<220> FEATURE:
<223> OTHER INFORMATION: Synthetic multiple antigenic agent
<220> FEATURE:
<221> NAME/KEY: MISC_FEATURE
<222> LOCATION: (1)..(1)
<223> OTHER INFORMATION: N-terminal amino group has attached R1 which is
      0 to 2 amino acid residues, wherein said amino acid residue may be
      a Gly or Cys, or a nucleic acid sequence.
<220> FEATURE:
<221> NAME/KEY: MISC_FEATURE
<222> LOCATION: (1)..(1)
<223> OTHER INFORMATION: Side chain amino group has attached R2 which is
      a B cell determinant, a T cell determinant, or a targeting
      molecule.
<220> FEATURE:
<221> NAME/KEY: MISC_FEATURE
<222> LOCATION: (3)..(3)
<223> OTHER INFORMATION: Side chain amino group has attached R3 which is
      a B cell determinant, a T cell determinant, or a targeting
      molecule.
<220> FEATURE:
<221> NAME/KEY: MISC_FEATURE
<222> LOCATION: (5)..(5)
<223> OTHER INFORMATION: "Xaa" represents 0 to 1 amino acid residue of
      Lys-R4 or Gly, wherein R4 is a B cell determinant, a T cell
      determinant, or a targeting molecule.
<220> FEATURE:
<221> NAME/KEY: MISC_FEATURE
<222> LOCATION: (5)..(5)
<223> OTHER INFORMATION: C-terminus has attached R5 group which is an
      amino acid, peptide, or nucleic acid sequence.

<400> SEQUENCE: 1

Lys Gly Lys Gly Xaa
1               5

<210> SEQ ID NO 2
<211> LENGTH: 14
<212> TYPE: PRT
<213> ORGANISM: Artificial Sequence
<220> FEATURE:
<223> OTHER INFORMATION: Synthetic multiple antigenic agent
<220> FEATURE:
<221> NAME/KEY: MISC_FEATURE
<222> LOCATION: (1)..(1)
<223> OTHER INFORMATION: Mannosylated residue
<220> FEATURE:
<221> NAME/KEY: MISC_FEATURE
<222> LOCATION: (2)..(2)
<223> OTHER INFORMATION: Mannosylated serine residue attached to side
      chain amino group
<220> FEATURE:
<221> NAME/KEY: MISC_FEATURE
<222> LOCATION: (4)..(4)
<223> OTHER INFORMATION: Mannosylated serine residue attached to side
      chain amino group
<220> FEATURE:
<221> NAME/KEY: MISC_FEATURE
<222> LOCATION: (6)..(6)
<223> OTHER INFORMATION: Mannosylated serine residue attached to side
      chain amino group
<220> FEATURE:
<221> NAME/KEY: MISC_FEATURE
<222> LOCATION: (8)..(8)
<223> OTHER INFORMATION: S1 peptide attached to side chain amino group
<220> FEATURE:
<221> NAME/KEY: MISC_FEATURE
<222> LOCATION: (10)..(10)
<223> OTHER INFORMATION: S2 peptide attached to side chain amino group
<220> FEATURE:
<221> NAME/KEY: MISC_FEATURE
<222> LOCATION: (12)..(12)
<223> OTHER INFORMATION: M2e24 peptide attached to side chain amino
      group
<220> FEATURE:
```

<221> NAME/KEY: MISC_FEATURE
<222> LOCATION: (12)..(12)
<223> OTHER INFORMATION: M2e24 peptide attached to side chain amino
      group

<400> SEQUENCE: 2

Ser Lys Gly Lys Gly Lys Gly Lys Gly Lys Gly Lys Gly Ala
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic multiple antigenic agent
<220> FEATURE:
<221> NAME/KEY: MISC_FEATURE
<222> LOCATION: (3)..(3)
<223> OTHER INFORMATION: Serine attached to side chain amino group
<220> FEATURE:
<221> NAME/KEY: MISC_FEATURE
<222> LOCATION: (5)..(5)
<223> OTHER INFORMATION: Serine attached to side chain amino group
<220> FEATURE:
<221> NAME/KEY: MISC_FEATURE
<222> LOCATION: (7)..(7)
<223> OTHER INFORMATION: S2 peptide attached to side chain amino group
<220> FEATURE:
<221> NAME/KEY: MISC_FEATURE
<222> LOCATION: (9)..(9)
<223> OTHER INFORMATION: S1 peptide attached to side chain amino group
<220> FEATURE:
<221> NAME/KEY: MISC_FEATURE
<222> LOCATION: (11)..(11)
<223> OTHER INFORMATION: M2e24 peptide attached to side chain amino
      group

<400> SEQUENCE: 3

Lys Gly Lys Gly Lys Gly Lys Gly Lys Gly Lys Gly Ala
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic multiple antigenic agent
<220> FEATURE:
<221> NAME/KEY: MISC_FEATURE
<222> LOCATION: (2)..(2)
<223> OTHER INFORMATION: Serine attached to side chain amino group
<220> FEATURE:
<221> NAME/KEY: MISC_FEATURE
<222> LOCATION: (4)..(4)
<223> OTHER INFORMATION: Serine attached to side chain amino group
<220> FEATURE:
<221> NAME/KEY: MISC_FEATURE
<222> LOCATION: (6)..(6)
<223> OTHER INFORMATION: Serine attached to side chain amino group
<220> FEATURE:
<221> NAME/KEY: MISC_FEATURE
<222> LOCATION: (8)..(8)
<223> OTHER INFORMATION: S1 peptide attached to side chain amino group
<220> FEATURE:
<221> NAME/KEY: MISC_FEATURE
<222> LOCATION: (10)..(10)
<223> OTHER INFORMATION: S2 peptide attached to side chain amino group
<220> FEATURE:
<221> NAME/KEY: MISC_FEATURE
<222> LOCATION: (12)..(12)
<223> OTHER INFORMATION: M2e24 peptide attached to side chain amino
      group

<400> SEQUENCE: 4

```
Ser Lys Gly Lys Gly Lys Gly Lys Gly Lys Gly Ala
1               5                   10
```

<210> SEQ ID NO 5
<211> LENGTH: 12
<212> TYPE: PRT
<213> ORGANISM: Artificial Sequence
<220> FEATURE:
<223> OTHER INFORMATION: Synthetic multiple antigenic agent
<220> FEATURE:
<221> NAME/KEY: MISC_FEATURE
<222> LOCATION: (2)..(2)
<223> OTHER INFORMATION: Serine residue attached to side chain
<220> FEATURE:
<221> NAME/KEY: MISC_FEATURE
<222> LOCATION: (4)..(4)
<223> OTHER INFORMATION: S2 peptide attached to side chain amino group
<220> FEATURE:
<221> NAME/KEY: MISC_FEATURE
<222> LOCATION: (6)..(6)
<223> OTHER INFORMATION: S1 peptide attached to side chain amino group
<220> FEATURE:
<221> NAME/KEY: MISC_FEATURE
<222> LOCATION: (8)..(8)
<223> OTHER INFORMATION: M2e24 peptide attached to side chain amino
      group
<220> FEATURE:
<221> NAME/KEY: MISC_FEATURE
<222> LOCATION: (10)..(10)
<223> OTHER INFORMATION: M2e24 peptide attached to side chain amino
      group

<400> SEQUENCE: 5

```
Ser Cys Gly Lys Gly Lys Gly Lys Gly Lys Gly Ala
1               5                   10
```

<210> SEQ ID NO 6
<211> LENGTH: 11
<212> TYPE: PRT
<213> ORGANISM: Artificial Sequence
<220> FEATURE:
<223> OTHER INFORMATION: Synthetic multiple antigenic agent
<220> FEATURE:
<221> NAME/KEY: MISC_FEATURE
<222> LOCATION: (3)..(3)
<223> OTHER INFORMATION: S1 peptide attached to side chain amino group
<220> FEATURE:
<221> NAME/KEY: MISC_FEATURE
<222> LOCATION: (5)..(5)
<223> OTHER INFORMATION: S2 peptide attached to side chain amino group
<220> FEATURE:
<221> NAME/KEY: MISC_FEATURE
<222> LOCATION: (7)..(7)
<223> OTHER INFORMATION: M2e24 peptide attached to side chain amino
      group
<220> FEATURE:
<221> NAME/KEY: MISC_FEATURE
<222> LOCATION: (9)..(9)
<223> OTHER INFORMATION: M2e24 peptide attached to side chain amino
      group

<400> SEQUENCE: 6

```
Cys Gly Lys Gly Lys Gly Lys Gly Lys Gly Ala
1               5                   10
```

<210> SEQ ID NO 7
<211> LENGTH: 11
<212> TYPE: PRT
<213> ORGANISM: Artificial Sequence
<220> FEATURE:
<223> OTHER INFORMATION: Synthetic multiple antigenic agent
<220> FEATURE:
<221> NAME/KEY: MISC_FEATURE
<222> LOCATION: (1)..(1)

```
<223> OTHER INFORMATION: Dimer created by disulfide linkage
<220> FEATURE:
<221> NAME/KEY: MISC_FEATURE
<222> LOCATION: (3)..(3)
<223> OTHER INFORMATION: S1 peptide attached to side chain amino group
<220> FEATURE:
<221> NAME/KEY: MISC_FEATURE
<222> LOCATION: (5)..(5)
<223> OTHER INFORMATION: S2 peptide attached to side chain amino group
<220> FEATURE:
<221> NAME/KEY: MISC_FEATURE
<222> LOCATION: (7)..(7)
<223> OTHER INFORMATION: M2e24 peptide attached to side chain amino
      group
<220> FEATURE:
<221> NAME/KEY: MISC_FEATURE
<222> LOCATION: (9)..(9)
<223> OTHER INFORMATION: M2e24 peptide attached to side chain amino
      group

<400> SEQUENCE: 7

Cys Gly Lys Gly Lys Gly Lys Gly Lys Gly Ala
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic multiple antigenic agent
<220> FEATURE:
<221> NAME/KEY: MISC_FEATURE
<222> LOCATION: (1)..(1)
<223> OTHER INFORMATION: M2e15 peptide attached to side chain amino
      group
<220> FEATURE:
<221> NAME/KEY: MISC_FEATURE
<222> LOCATION: (3)..(3)
<223> OTHER INFORMATION: M2e15 peptide attached to side chain amino
      group
<220> FEATURE:
<221> NAME/KEY: MISC_FEATURE
<222> LOCATION: (5)..(5)
<223> OTHER INFORMATION: S1 peptide attached to side chain amino group
<220> FEATURE:
<221> NAME/KEY: MISC_FEATURE
<222> LOCATION: (7)..(7)
<223> OTHER INFORMATION: S2 peptide attached to side chain amino group
<220> FEATURE:
<221> NAME/KEY: MISC_FEATURE
<222> LOCATION: (9)..(9)
<223> OTHER INFORMATION: M2e15 peptide attached to side chain amino
      group
<220> FEATURE:
<221> NAME/KEY: MISC_FEATURE
<222> LOCATION: (11)..(11)
<223> OTHER INFORMATION: M2e15 peptide attached to side chain amino
      group

<400> SEQUENCE: 8

Lys Gly Lys Gly Lys Gly Lys Gly Lys Gly Lys Gly Ala
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic S1 peptide

<400> SEQUENCE: 9

Ser Phe Glu Arg Phe Glu Ile Phe Pro Lys Glu
1               5                   10
```

```
<210> SEQ ID NO 10
<211> LENGTH: 13
<212> TYPE: PRT
<213> ORGANISM: Artificial Sequence
<220> FEATURE:
<223> OTHER INFORMATION: Synthetic S2 peptide

<400> SEQUENCE: 10

His Asn Thr Asn Gly Val Thr Ala Ala Ser Ser His Glu
1               5                   10

<210> SEQ ID NO 11
<211> LENGTH: 24
<212> TYPE: PRT
<213> ORGANISM: Artificial Sequence
<220> FEATURE:
<223> OTHER INFORMATION: Synthetic M2e24 peptide

<400> SEQUENCE: 11

Ser Leu Leu Thr Glu Val Glu Thr Pro Ile Arg Asn Glu Trp Gly Cys
1               5                   10                  15

Arg Ser Asn Asp Ser Ser Asp Pro
            20

<210> SEQ ID NO 12
<211> LENGTH: 15
<212> TYPE: PRT
<213> ORGANISM: Artificial Sequence
<220> FEATURE:
<223> OTHER INFORMATION: Synthetic M2e15 peptide
<220> FEATURE:
<221> NAME/KEY: MISC_FEATURE
<222> LOCATION: (9)..(9)
<223> OTHER INFORMATION: Xaa denotes either Pro, His, or Leu

<400> SEQUENCE: 12

Ser Leu Leu Thr Glu Val Glu Thr Xaa Ile Arg Asn Glu Trp Gly
1               5                   10                  15

<210> SEQ ID NO 13
<211> LENGTH: 8
<212> TYPE: PRT
<213> ORGANISM: Artificial Sequence
<220> FEATURE:
<223> OTHER INFORMATION: Synthetic multiple antigenic agent

<400> SEQUENCE: 13

Cys Gly Lys Gly Lys Gly Lys Ala
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic multiple antigenic agent
<220> FEATURE:
<221> NAME/KEY: MISC_FEATURE
<222> LOCATION: (3)..(3)
<223> OTHER INFORMATION: M2e24 petide attached to side chain amino
      group
<220> FEATURE:
<221> NAME/KEY: MISC_FEATURE
<222> LOCATION: (5)..(5)
<223> OTHER INFORMATION: M2e24 petide attached to side chain amino
      group
```

```
<400> SEQUENCE: 14

Cys Gly Lys Gly Lys Gly Lys Ala
1               5
```

MULTIPLE ANTIGENIC AGENTS AND METHODS FOR USING THE SAME

This application is a Continuation-in-Part Application of U.S. patent application Ser. No. 10/757,692 filed Jan. 14, 2004 now abandoned, which claims the benefit of priority from U.S. provisional application Ser. No. 60/441,374, filed on Jan. 16, 2003, each of which are herein incorporated by reference in their entireties.

INTRODUCTION

This invention was made in the course of research sponsored by the National Institute of Allergy and Infectious Disease (NIAID Grant Nos. AI-46457 and AI-13989). The U.S. government may have certain rights in this invention.

BACKGROUND OF THE INVENTION

Three types of transmembrane proteins are expressed in the membrane of influenza type A virions and virus-infected cells. The hemagglutinin and neuraminidase are glycoproteins with large ectodomains of ~510 and ~420 amino acids, respectively. Hemagglutinin is assembled as homotrimers and neuraminidase as homotetramers forming a dense layer of 13-14 nm long, rod-shaped surface projections on the viral membrane and at cellular sites of virus maturation. Current influenza virus vaccines aim at inducing a strong antibody response to these glycoproteins, particularly the hemagglutinin, as such antibodies are well-known to be highly protective against infection. The problem is that influenza type A virus has a high propensity for changing the determinants recognized by these protective antibodies, which necessitates repetitive vaccination with updated vaccine strains that reflect these antigenic changes. By contrast, the third viral transmembrane protein, matrix protein 2 (M2), contains an ectodomain (M2e) that is conserved amongst human influenza virus strains. Broad protective immunity against influenza type A virus infection using M2 has been investigated (Slepushkin, et al. (1995) *Vaccine* 13:1399-1402; Frace, et al. (1999) *Vaccine* 17:2237-44; Neirynck, et al. (1999) *Nature Med.* 5:1157-63; Okuda, et al. (2001) *Vaccine* 19:3681-91).

M2 is a 97 amino acid long transmembrane protein of influenza type A virus (Lamb, et al. (1981) *Proc. Natl. Acad. Sci. USA* 78:4170-4174; Lamb, et al. (1985) *Cell* 40:627-633). The mature protein forms homotetramers (Holsinger and Lamb (1991) *Virology* 183:32-43; Sugrue and Hay (1991) *Virology* 180:617-624) that have pH-inducible ion channel activity (Pinto, et al. (1992) *Cell* 69:517-528; Sugrue and Hay (1991) supra). M2-tetramers are expressed at high density in the plasma membrane of infected cells but are relatively excluded from sites of virus maturation and therefore are incorporated only at a low frequency into the membrane of mature virus particles (Takeda, et al. (2003) *Proc. Natl. Acad. Sci. USA* 100:14610-14617; Zebedee and Lamb (1988) *J. Virol.* 62:2762-2772). The sequence of the 24 amino acid long ectodomain of M2 (M2e) has remained conserved amongst human epidemic virus strains (Macken, et al. (2001) In Options for the Control of Influenza. IV. Osterhaus, et al. (ed.), p. 103-106. Elsevier Science, Amsterdam). The majority of human epidemic strains isolated since 1918 share the same M2e protein sequence. Further, several studies in mice have shown that M2e-specific antibodies restrict influenza virus replication and reduce morbidity and mortality (Fan, et al. (2004) *Vaccine* 22:2993-3003; Liu, et al. (2004) *Immunol. Lett.* 93:131-136; Mozdzanowska, et al. (2003) *J. Virol.* 77:8322-8328; Neirynck, et al. (1999) supra; Treanor, et al. (1990) *J. Virol.* 64:1375-1377). Moreover, in ferrets, the animal model considered most prognostic for human influenza, protective activity of M2e-specific immunity has been demonstrated (Fan, et al. (2004) supra) and sera from rhesus monkeys immunized with a M2e-carrier conjugate have been shown to exhibit protective activity upon transfer into mice (Fan, et al. (2004) supra). Thus, with the exception of a study in pigs, which indicated that M2e-specific immunity may enhance rather than ameliorate disease (Heinen, et al. (2002) *J. Gen. Virol.* 83:1851-1859), evidence from animal models shows that M2e-specific immunity is capable of providing a significant level of protection that is directed against a remarkably conserved viral target.

The low degree of structural variation in M2e is certainly in part attributable to constraints resulting from its genetic relation to M1, the most conserved protein of the virus (Ito, et al. (1991) *J. Virol.* 65:5491-5498). M2 is encoded by a spliced RNA of the viral gene segment 7, which codes also for M1 (Lamb, et al. (1985) supra). The splicing event removes most of the nucleotides that code for M1 (nt 27-714) except the 26 most 5' and 42 most 3' nucleotides (Lamb, et al. (1985) supra). Thus, nucleotides 1-68 of M2 which encode essentially the entire M2e are bicistronic, from 1-26 in the same and from 27-68 in a different reading frame. This genetic relation between M2e and M1 can be expected to substantially restrict the degree of variability in M2e. An additional factor that may contribute to the low degree of change seen in M2e amongst human influenza virus strains could be the absence of M2e-specific antibodies and thus pressure for change. A small study of 17 paired human sera obtained during the acute and convalescent phase of natural infection found that M2-specific antibodies were absent from acute sera and became detectable in only six of the convalescents (Black, et al. (1993) *J. Gen. Virol.* 74 (Pt 1):143-146). This was in contrast to nucleoprotein-specific antibody titers, which increased in 15 of 17 convalescent sera, thus confirming recent influenza infection of the donors (Black, et al. (1993) supra). Another study found no difference in M2e-specific antibody titers in two larger groups of unpaired sera, one positive and the other negative for virus-specific antibodies (Liu, et al. (2003) *FEMS Immunol. Med. Microbiol.* 35:141-146). These data suggest that while infection in humans can result in a measurable antibody response to M2, the response is not generated consistently and is small and of short duration. Similar observations have been made in the mouse model where two repetitive infections with virus strains that shared the same M2e induced only low titers of M2e-specific antibodies (Mozdzanowska, et al. (2003) *Vaccine* 21:2616-2626). Since M2 is a minor component (<0.5%) of purified virus (Zebedee and Lamb (1988) *J. Virol.* 62:2762-2772), inactivated influenza virus vaccines presently being used would not be expected to induce M2e-specific immunity either.

M2e-specific monoclonal antibody 14C2 does not prevent virus infection in vitro but reduces virus yield and plaque size when incorporated into the culture medium or agar overlay (Zebedee and Lamb (1988) supra; Hughey, et al. (1995) *Virology* 212:411-21). Not all M2e-specific antibodies display this activity (Hughey, et al. (1995) supra) and not all virus strains are susceptible to it (Zebedee and Lamb (1988) supra). In vivo, passive monoclonal antibody 14C2 similarly decreases virus growth (Treanor, et al. (1990) *J. Virol.* 64:1375-7) and is effective also against PR8 (Mozdzanowska, et al. (1999) *Virology* 254:138-46), which is not susceptible to antibody-mediated growth restriction in vitro (Zebedee and Lamb (1988) supra; Mozdzanowska, et al. (1999) supra), indicating that antibody-mediated virus growth-inhibition occurs through distinct mechanisms in vitro and in vivo.

It has now been found that a multiple antigenic agent containing M2e linked to helper T cell determinants is an effective vaccine for inducing virus protection. M2e-MAAs together with cholera toxin (CT) and a synthetic oligodeoxynucleotide (ODN) with a stimulatory CpG motif induces strong M2e-specific antibody titers in serum of mice and results in significant protection against influenza virus challenge.

SUMMARY OF THE INVENTION

The present invention is a multiple antigenic agent (MAA) of the structure:

$$R_1\text{-}(Lys\text{-}Gly)_m\text{-}(Lys\text{-}Gly)_n\text{-}Xaa_1\text{-}R_5 \quad \text{Formula I}$$
$$\qquad\;\;|\qquad\qquad\;\;|$$
$$\qquad R_2\qquad\quad R_3$$

(SEQ ID NO:1) wherein, $R_1$ is 0 to 2 amino acid residues comprising Cys or Gly or a nucleic acid sequence; m is at least 1; n is at least 1; $Xaa_1$ is 0 to 1 amino acid residue comprising $$\text{Lys}$$
$$|$$
$$R_4$$

or Gly; $R_2$, $R_3$, and $R_4$ may independently be a B cell determinant, a T cell determinant, or a targeting molecule; and $R_5$ is an amino acid, peptide, or nucleic acid sequence. In one embodiment, when m is greater than 1, each $R_2$ can independently be a B cell determinant, a T cell determinant, or a targeting molecule; and when n is greater than 1, each $R_3$ can independently be a B cell determinant, a T cell determinant, or a targeting molecule. In a particular embodiment, the B cell determinant is the ectodomain of matrix protein 2, or a fragment or homolog thereof. In another embodiment, a Cys residue located at the N-terminus of a first MAA is covalently linked via a disulfide bond to a second Cys residue at the N-terminus of a second MAA of Formula I to produce an MAA dimer of Formula I.

The present invention is also a composition containing an MAA and a pharmaceutically acceptable carrier. In one embodiment, the composition containing the MAA and the pharmaceutically acceptable carrier may further contain an adjuvant. Such compositions are useful for preventing or treating a viral infection. Accordingly, a method for preventing or treating a viral infection is provided involving administering to a susceptible subject or one exhibiting signs or symptoms of viral infection an effective amount of a composition of the invention to prevent or treat the signs or symptoms of a viral infection. In particular embodiment, the viral infection is influenza type A virus.

These and other aspects of the present invention are set forth in more detail in the following description of the invention.

BRIEF DESCRIPTION OF THE DRAWINGS

FIG. 1 shows the effects of M2e-MAA dose on M2e antibody titer. BALB/c mice were immunized i.n. with the indicated doses of an MAA containing four M2e24 B cell determinants in adjuvant. M2e-specific serum antibody titers were determined three weeks after each immunization. Mean values from two independent experiments are shown.

FIG. 2 shows specificity of the response induced by immunization with (4)M2e-MAA. FIG. 2A, groups of four mice were immunized with the same dose of (4)M2e25-MAA in adjuvant by the i.n., s.c. or i.p. route. Sera obtained after first and second booster immunizations were tested for specificity by ELISA for antibody titer at 21 days after the first booster immunization (b21), 14 days after the second booster immunization (2b14), and 90 days after the second booster immunization (2b90). Binding to each immunosorbent was quantified by comparison to the binding seen with purified anti-M2e monoclonal antibody.

DETAILED DESCRIPTION OF THE INVENTION

It has now been found that animals, inoculated with multiple antigenic agents (MAAs) containing multiple B cell determinants and T helper cell (Th) determinants, exhibit significant resistance against subsequent challenge with infectious virus. As defined herein, a multiple antigenic agent is an agent which contains more than one peptide or nucleic acid moiety which is capable of inducing a specific immune response in an animal. The B cell determinant induces an antibody response and can also induce a T cell response. The advantage of the MAAs provided herein is that a multitude of antigenic side chains can be attached to the core peptide, which contains Lys-Gly repeats, thereby enabling presentation of several structurally linked determinants. Furthermore, when a Cys residue is linked at the N-terminus of the core peptide, two core peptides can be covalently linked via disulfide bonds to effectively double the number of antigenic side chains and hence improve immune responses in mammals. Further, as the MAA provided herein can be readily chemically synthesized, the production of the MAA is highly controlled and contaminants are minimized.

Accordingly, the present invention is an MAA of the structure:

$$R_1\text{-}(Lys\text{-}Gly)_m\text{-}(Lys\text{-}Gly)_n\text{-}Xaa_1\text{-}R_5 \quad \text{Formula I}$$
$$\qquad\;\;|\qquad\qquad\;\;|$$
$$\qquad R_2\qquad\quad R_3$$

(SEQ ID NO:1), wherein m is at least 1 and n is at least 1. In one embodiment, the summation of m and n is about 10 to 30. In another embodiment the summation of m and n is about 10.

In the MAA of Formula I, the amino acid moiety $Xaa_1$ is 0 to 1 amino acid residue, wherein when $Xaa_1$ is 1 amino acid residue, the amino acid is or Gly. In particular embodiments, $Xaa_1$ is Gly.

In the MAA of Formula I, the $R_1$ moiety is 0 to 2 amino acid residues or a nucleic acid sequence such as an oligodeoxynucleotide (ODN) with a stimulatory CpG motif. In one embodiment, the $R_1$ moiety is 0 amino acid residues. In another embodiment, the $R_1$ moiety is 1 amino acid residue. When $R_1$ is 1 amino acid residue, the amino acid residue can be a Gly or Cys. In yet another embodiment, $R_1$ is the dipeptide Cys-Gly. When the N-terminal amino acid of a first MAA is a Cys-Gly dipeptide, the Cys residue is desirably covalently linked to a second Cys residue at the N-terminus of a second MAA of Formula I. The disulfide linkage between the first and second cysteine residues generates a covalently linked MAA dimer of Formula I. It is contemplated that the peptides of the dimer can be identical or differ in the number of Lys-Gly repeats (i.e., the number of m and n), $Xaa_1$, $R_2$, $R_3$, $R_4$ or $R_5$.

In the MAA of Formula I, the $R_2$, $R_3$ and $R_4$ substituents attached to the ε-amino group of lysine can independently be a B cell determinant, a T cell determinant, or a targeting molecule. In one embodiment, at least one B cell determinant and one T cell determinant are present in the MAA of Formula I. In another embodiment, the MAA of Formula I has at least two B cell determinants. In still a further embodiment, the MAA of Formula I has at least four B cell determinants. Advantageously, the MAA of Formula I can have various combinations and numbers of B cell determinants, T cell determinants, or targeting molecules from various sources (e.g., from different viral families or serotypes). To illustrate, a monomer MAA of the invention can contain five B cell determinants, two T cell determinants and two targeting molecule side chains. Alternatively, a monomer MAA of the invention can, for example, contain eight B cell determinants, one T cell determinant and one targeting molecule side chain. The combinations are not particularly limited and can vary with the selected B cell determinant, T cell determinant or targeting molecule. Further, individual R groups of Lys-Gly repeats of m or n length can vary. For example, if m=3, $R_2$ of the first Lys-Gly repeat can be a B cell determinant, the $R_2$ of the second Lys-Gly repeat can be a T cell determinant and the $R_2$ of the third Lys-Gly repeat can be a targeting molecule.

B cell determinants, as used herein, desirably elicit a measurable B cell response as determined by, for example, production of antibodies to the native viral protein. B cell determinants which can be used in the MAA of Formula I include those already known in the art as well as any other antigens such as glycans, polypeptides, or nucleic acids which elicit a B cell response. In one embodiment, antigens are derived from enveloped or non-enveloped viruses. In another embodiment, antigens are derived from viruses including, but not limited to, those from the family Adenoviridae, Arenaviridae (e.g., Lymphocytic choriomeningitis virus), Arterivirus (e.g., Equine arteritis virus), Astroviridae (Human astrovirus 1), Birnaviridae (e.g., Infectious pancreatic necrosis virus, Infectious bursal disease virus), Bunyaviridae (e.g., California encephalitis virus Group), Caliciviridae (e.g., Caliciviruses), Coronaviridae (e.g., Human coronaviruses 299E and OC43), Deltavirus (e.g., Hepatitis delta virus), Filoviridae (e.g., Marburg virus, Ebola virus Zaire), Flaviviridae (e.g., Yellow fever virus group, Hepatitis C virus), Hepadnaviridae (e.g., Hepatitis B virus), Herpesviridae (e.g., Epstein-Bar virus, Simplexvirus, Varicellovirus, Cytomegalovirus, Roseolovirus, Lymphocryptovirus, Rhadinovirus), Orthomyxoviridae (e.g., Influenzavirus A, B, and C), Papovaviridae (e.g., Papillomavirus), Paramyxoviridae (e.g., Paramyxovirus such as human parainfluenza virus 1, Morbillivirus such as Measles virus, Rubulavirus such as Mumps virus, Pneumovirus such as Human respiratory syncytial virus), Picornaviridae (e.g., Rhinovirus such as Human rhinovirus 1A, Hepatovirus such Human hepatitis A virus, Human poliovirus, Cardiovirus such as Encephalomyocarditis virus, Aphthovirus such as Foot-and-mouth disease virus O, Coxsackie virus), Poxyiridae (e.g., Orthopoxvirus such as Variola virus), Reoviridae (e.g., Rotavirus such as Groups A-F rotaviruses), Retroviridae (Primate lentivirus group such as human immunodeficiency virus 1 and 2), Rhabdoviridae (e.g., rabies virus) and Togaviridae (e.g., Rubivirus such as Rubella virus).

An exemplary B cell determinant which can be used in the MAA of Formula I includes, but is not limited to, the ectodomain of M2, or a fragment or homolog thereof. In one embodiment, the B cell determinant of the MAA of Formula I is M2e derived from influenza type A set forth herein as SEQ ID NO:11. In a particular embodiment, the B cell determinant of the MAA of Formula I is an M2e fragment represented by SEQ ID NO:12. In still further embodiments, the B cell determinant of the MAA of Formula I is a homolog of M2e derived from viral transmembrane proteins such as NB of influenza type B virus or CM2 of influenza type C virus.

T cell determinants are intended to include both Th and cytotoxic T cell determinants. Elicitation of T cell responses can be detected, for example, as exemplified herein or by measuring the production of cytokines, e.g., IFN-gamma, IL-2, IL-4, IL-5, or IL-10. Exemplary T cell determinants which can be used in the MAA of Formula I include, but are not limited to, hemagglutinin T cell determinants and T cell determinants restricted to human MHC class II proteins, preferably to a broad range of haplotypes.

Targeting molecules covalently linked to the antigen as the $R_2$, $R_3$, or $R_4$ moieties are, in general, carbohydrates, lipids, peptides or oligonucleotides which deliver the antigen to the desired site. Targeting molecules which can be incorporated into the MAAs of the present invention include, but are not limited to, cholera toxin, ODNs with stimulatory CpG motifs (see, e.g., Shirota, et al. (2001) *J. Immunol.* 167(1):66-74) and endogenous human immunomodulators, such as IL-2, IL-12, and GM-CSF.

The $R_5$ moiety of the MAA of Formula I is not particularly limited and can be any amino acid (e.g., β-linked alanine), peptide, or nucleic acid sequence such as an ODN with a stimulatory CpG motif.

The MAA of Formula I can be prepared in accordance with the methods exemplified herein or any other suitable method of chemically synthesizing peptides and peptide conjugates. Wherein nucleic acid sequences are incorporated into Formula I, said nucleic acid sequences can be attached via spacer or linker molecules such as hydroxycarboxylic acid.

Examples provided herein disclose various derivatives of the MAA of Formula I for inducing an immune response in mice (see Table 1) and are intended to illustrate and not limit the scope of the invention. Other aspects, advantages and modifications within the scope of the invention will be apparent to those skilled in the art to which the invention pertains.

M2e-MAAs were administered to anesthetized mice by the intranasal (i.n.) route in a dose of 50 µL. Primary and booster inocula contained 3 µg of MAA, 3 µg of phosphorothionated oligodeoxynucleotide (ODN) 1826, which contains an immunostimulatory CpG motif, and 0.5 µg of cholera toxin (CT) in phosphate-buffered saline (PBS) and were given at an interval of four to five weeks. Mice inoculated i.n. with ODN and CT alone or with infectious virus were used as negative and positive controls, respectively. In the latter case, the first infection was with PR8 and the second with PR8-SEQ14, a variant that differs from PR8 by 14 amino acid substitutions in hemagglutinin-determinants recognized by protective monoclonal antibodies and can readily induce an infection in PR8-immune mice.

Ten to thirty days after boost, cells from mediastinal lymph nodes (MedLNs) were tested for their capacity to proliferate in response to free S1 peptide, hemagglutinin and M2e. Cells from spleen and lymph nodes draining the upper respiratory tract gave smaller responses and were less extensively studied. The responses of M2e-MAA-immunized mice consistently exceeded those of adjuvant-primed control mice. Only two of the data sets exceeded the response of the control mice on a statistical basis (paired t test, $p \geq 0.05$). However, as a group, M2e-MAA-immunized mice exhibited significantly greater S1- and hemagglutinin-specific responses than control mice (unpaired t test, $p \leq 0.05$). The hemagglutinin-specific response of M2e-MAA-immunized mice was similar in size to the one of infection-immunized mice but differed in fine specificity in that S1-specific Th were detected in M2e-MAA-immunized but not infection-immunized mice. The mannosylated MAA was not superior to non-mannosylated MAAs in inducing a S1-specific Th response in vivo, in marked in contrast to its greater stimulatory potency in vitro. Further, M2e-MAA-immunized but not infection-immunized mice contained M2e-specific proliferative T cells, indicating that M2e itself contains at least one $H2^d$-restricted Th determinant.

There was no evidence of induction of MHC class I-restricted cytotoxic memory T (Tc) responses by M2e-MAAs, which is consistent with the absence of a characteristic $K^d$-restriction, $D^d$-restriction or $L^d$-restriction motif in M2e (Engelhard (1994) Curr. Opin. Immunol. 6:13-23; Corr, et al. (1993) J. Exp. Med. 178:1877-92). Memory Tc were readily detectable in infection-immunized mice.

M2e-specific serum antibody titers were measured by ELISA on solid phase immunoadsorbents of (1)M2e24-MAA and JAP-MDCK cell monolayers. Each assay was standardized and quantified by concomitant titration of purified M2e-specific monoclonal antibody 14C2 and antibody titers in test samples were defined as equivalent µg M2e-specific antibody per milliliter of serum.

Combined data from four independent immunization experiments in which mice were bled 2 and 4 weeks after priming, 2 and 4-5 weeks after second and 2 and 5 weeks after the third immunization provided the average and SEM of group titers from the different immunization experiments. The data indicated that constructs containing four B cell determinants (e.g., (4)M2e24-MAA) induced a prompter and stronger response than the constructs containing two B cell determinants (e.g., (2)M2e24-MAA) and the latter was superior to constructs containing one B cell determinant (e.g., (1)M2e24-MAA). Unexpectedly, and in contrast to the enhanced stimulation of Th cells in vitro, mannosylation decreased the MAA's ability to induce an antibody response in vivo. This held for both the antibody titer measured against a construct containing one M2e24 (i.e., (1)M2e24-MAA) and JAP-MDCK cells. Immunization with constructs containing four M2e24 B cell determinants consistently induced significant antibody titers two weeks after the second immunization and sometimes induced a significant response as soon as four weeks after primary immunization (in four independent experiments, mean titers of 1.0, 2.0, 4.6, and 1035 µg/mL 4 weeks after first immunization). The findings indicate that a multimeric presentation of M2e enhanced the B cell response, by facilitating the cross-linking of membrane Ig on M2e-specific B cells (Bachmann and Zinkernagel (1997) Annu. Rev. Immunol. 15:235-70).

Figure 1:
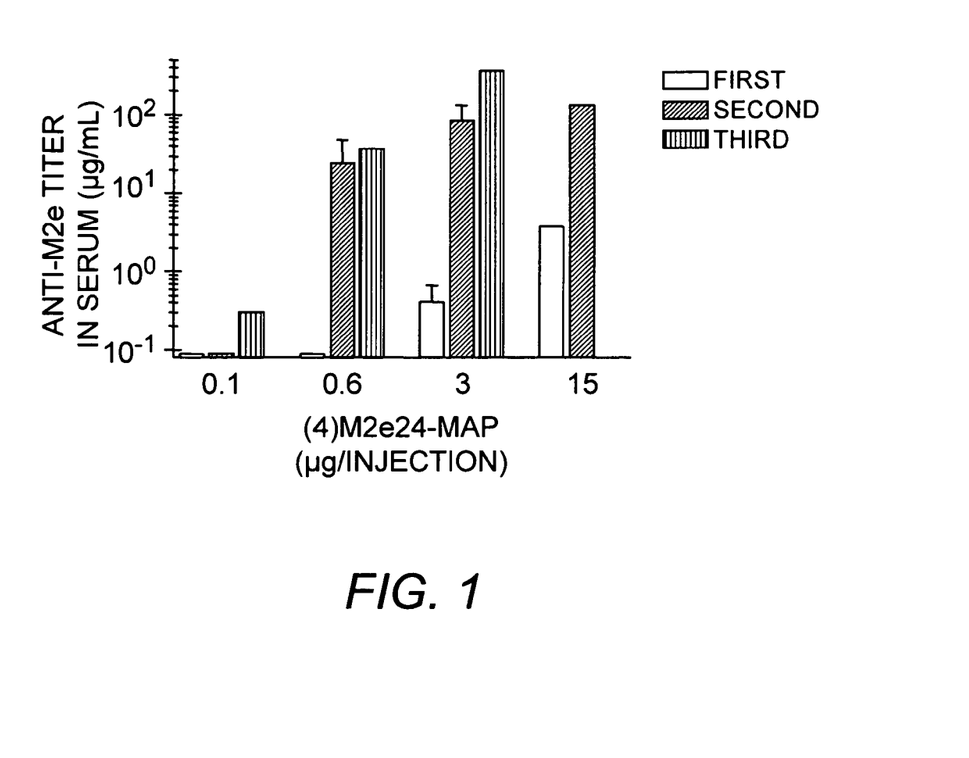

A dose of ~3 µg of M2e-MAA administered i.n. with adjuvant induced an optimal response as compared to doses of 0.1, 0.6 and 15 µg. The ~3 µg dose induced a minor primary response but a substantial secondary and tertiary antibody response (FIG. 1). The tertiary response was more uniform in terms of titer than the secondary response and was of long duration (>60 weeks). However, a dose as little as 0.6 µg induced a sizable secondary antibody response (FIG. 1).

The data further indicated that sera from M2e-MAA-immunized mice consistently exhibited higher titers against M2e-MAA than against JAP-MDCK cells. The ratio of M2e-MAA versus JAP-MDCK reactive antibodies in sera showed an average of 10 and ranged in individual sera from two to 31. This indicates that the specificity of the antibody response after M2e-MAA immunization differed amongst individual mice and that on average ~10% of the M2e-MAA specific antibodies cross-reacted with virus-induced M2e on infected cells. The residual antibodies may be directed to Th-determinants, scaffold peptide, determinants on the synthetic M2e-peptide that are not shared by the virus-induced M2-tetramer or combinations of these structures.

ELISA against M2e-MAA further indicated that sera from virus-infected mice contained very low M2e-specific antibody titers. The ELISA against JAP-MDCK detects antibodies to many viral proteins and was therefore not used to quantify the M2-specific response in infection-immunized mice. The only exception was one group of mice that had been immunized by three consecutive infections, first by PR8, second by JAP and third by X31 and exhibited a M2e-MAA-specific titer of ~30 µg/mL, which was in the same range as the viral M2e-specific antibody titers (versus JAP-MDCK) seen in mice immunized with (4)M2e24-MAA. The data showed that (4)M2e-MAA was more effective than virus infection in inducing a M2e-specific antibody response.

M2e-specific immune effectors were virtually absent from mice immunized by two consecutive infections. This is unexpected, considering that M2 is expressed at high density in the plasma membrane of infected cells (Lamb, et al. (1985) supra; Zebedee and Lamb (1988) supra) and that a vast number of epithelial cells become infected in the course of a total respiratory tract infection (Yilma, et al. (1979) *J. Inf. Disease* 139:458-64). This finding indicates that the strength of heterosubtypic protection may be enhanced by concomitant induction of the effectors induced by infection and M2e-specific vaccination.

Four to five weeks after the second immunization, mice were challenged with X31 and virus titer in nasal, tracheal and pulmonary tissues determined three days later. At this time, virus titer is affected almost exclusively by innate and extant memory defense activities as naïve SCID and immunocompetent mice show no difference in virus titer at this time point after challenge. Mice immunized with MAAs that contained a single M2e, with or without mannose, exhibited no significant resistance (ns, p>0.01 by student t test) to virus replication in nasal and pulmonary tissues but showed reduced virus replication in the trachea compared to mice primed with adjuvant alone. Conversely, in mice primed and boosted with (4)M2e24-MAA, the virus titer in nose, trachea and lung three days after total respiratory tract challenge was reduced on average by 10- to 100-fold compared to mice immunized with adjuvant alone. The protection was of similar strength in nose and trachea as seen in infection-immunized mice but of lesser strength in the lung when assessed 4 weeks after the boost. However, since infection-induced protection is largely memory T cell-mediated and appears to be of shorter duration than antibody-mediated protection, M2e-MAA-induced protection may be of longer duration than infection-induced protection.

Co-administration of (4)M2e24-MAA and infectious virus resulted in a slight increase in protection in nose and trachea but not lung, compared to mice immunized with (4)M2e24-MAA or infection alone. However, while infection increased the fraction of G2a antibodies, it decreased the size of the total M2e-specific antibody response in serum; serum antibody is known to play an important role in protection in the lung and less so in the nose and trachea.

M2e-specific serum antibody titers were tested in individual mice for correlation with virus titers. Antibody titers and nasal and pulmonary, but not tracheal, virus titers correlated inversely in (4)M2e-MAA-immunized mice (correlation coefficient, $R^2$, for nose and lung 0.53 and 0.51, respectively, $p<0.001$). However, a substantial fraction of the correlation was due to the single, outlying mouse that contained ~90 µg anti-M2e antibody per mL of serum. Its exclusion reduced the correlation between antibody and virus titer to an insignificant value in the nose but not in the lung, where it remained significant ($R^2$ 0.41, $p=0.002$). No correlation was seen between M2e-specific antibody and virus titers in trachea and in mice immunized by infection.

Figure 2A:
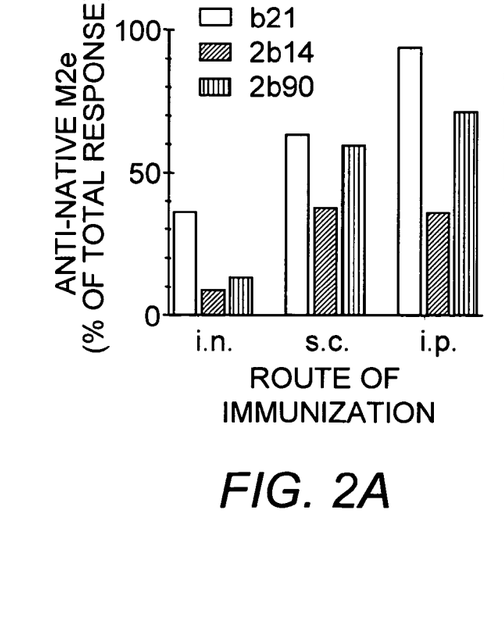
Figure 2B:
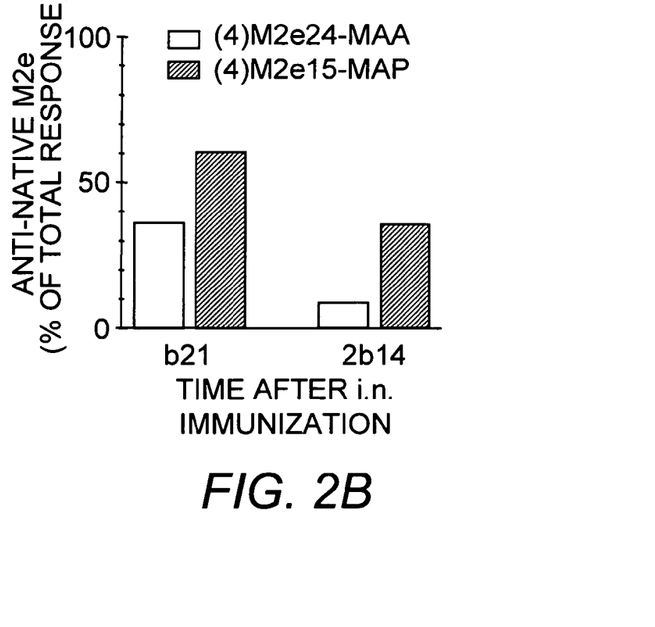
FIG. 2B, groups of four mice were immunized by the i.n. route with (4)M2e24-MAP or (4)M2e15-MAP in adjuvant and sera tested for specificity as in FIG. 2B.

Intranasal immunization with (4)M2e24-MAA in adjuvant induced antibodies of three main specificities: M2e-specific antibodies that cross-reacted with native M2e; M2e-peptide-specific antibodies that did not react with native M2e, and antibodies that were specific for determinants of M2e-MAAs other than M2e. These responses were assessed in ELISA against (2)M2e24-MAP, which provides a measure for the total response; Cys-M2e24, which provides an estimate for the M2e- and backbone-specific response; virus-infected MDCK cells, which measures the antibody titer to native M2e; and Cys-bb, which measures the response to MAA backbone (and assay background). On average, one-third of the response was directed to Th determinants and background, two-thirds (66±17%) was specific for M2e and approximately one-fifth (17±11%, SD; n=12) for native M2e. The response to native M2e can be further improved by using extrapulmonary routes of immunization (FIG. 2A) and M2e-MAAs that have C-terminal truncations (FIG. 2B).

The isotype composition of the M2e-specific antibody response induced by i.n. immunization with (4)M2e24-MAA was dominated by IgG1, an isotype that is less protective in the case of M2e-specific antibodies than IgG2a. Administration of M2e-MAA concomitantly with 100 $TCID_{50}$ of infectious PR8 (or PR8-Seq14) virus resulted in an increase of G2a and decrease of G1 isotype; however, the total size of the response was concomitantly reduced.

These results indicate that i.n. immunization with M2e-MAA in adjuvant provided significant protection that was almost as strong as the heterosubtypic protection resulting from two consecutive total respiratory tract infections. Further, M2e-specific protection can be further enhanced by increasing antibody titer (i.e., three instead of two injections), fraction of native M2e-specific antibody (i.e., truncation of C-terminal and extrapulmonary routes of immunization) and by biasing the isotype composition to G2a.

Given these results, the present invention is also a method for using the MAAs both as therapeutic and prophylactic agents for treating or preventing viral infections. In general, this will involve administering an effective amount of one or more MAAs of the present invention in a suitable form to a susceptible subject or one exhibiting signs or symptoms of viral infection.

As will be appreciated by the skilled artisan, the selection of the B cell determinant for the MAA of Formula I will be dependent on the viral infection to be prevented or treated. For example, to prevent or treat an influenza viral infection, the B cell determinant of the MAA of Formula I should be derived from influenza virus (e.g., M2e). In using cognate B cell determinants, it is contemplated that the MAA of Formula I will be effective in generating an immune response against enveloped or non-enveloped viruses including, but not limited to, those from the family Adenoviridae, Arenaviridae (e.g., Lymphocytic choriomeningitis virus), Arterivirus (e.g., Equine arteritis virus), Astroviridae (Human astrovirus 1), Birnaviridae (e.g., Infectious pancreatic necrosis virus, Infectious bursal disease virus), Bunyaviridae (e.g., California encephalitis virus Group), Caliciviridae (e.g., Caliciviruses), Coronaviridae (e.g., Human coronaviruses 299E and OC43), Deltavirus (e.g., Hepatitis delta virus), Filoviridae (e.g., Marburg virus, Ebola virus Zaire), Flaviviridae (e.g., Yellow fever virus group, Hepatitis C virus), Hepadnaviridae (e.g., Hepatitis B virus), Herpesviridae (e.g., Epstein-Bar virus, Simplexvirus, Varicellovirus, Cytomegalovirus, Roseolovirus, Lymphocryptovirus, Rhadinovirus), Orthomyxoviridae (e.g., Influenzavirus A, B, and C), Papovaviridae (e.g., Papillomavirus), Paramyxoviridae (e.g., Paramyxovirus such as human parainfluenza virus 1, Morbillivirus such as Measles virus, Rubulavirus such as Mumps virus, Pneumovirus such as Human respiratory syncytial virus), Picornaviridae (e.g., Rhinovirus such as Human rhinovirus 1A, Hepatovirus such Human hepatitis A virus, Human poliovirus, Cardiovirus such as Encephalomyocarditis virus, Aphthovirus such as Foot-and-mouth disease virus O, Coxsackie virus), Poxyiridae (e.g., Orthopoxvirus such as Variola virus), Reoviridae (e.g., Rotavirus such as Groups A-F rotaviruses), Retroviridae (Primate lentivirus group such as human immunodeficiency virus 1 and 2), Rhabdoviridae (e.g., rabies virus) and Togaviridae (e.g., Rubivirus such as Rubella virus).

Treatment of individuals having a viral infection involves identifying a subject exhibiting signs or symptoms of a viral infection and administering to said subject an effective amount of a MAA of Formula I of the present invention thereby decreasing the signs or symptoms associated with the viral infection or abbreviating the duration of the viral infection when compared to a subject who has not received treatment. Signs or symptoms of a viral infection are generally dependent on the particular virus and are well-known to the skilled clinician. For example, typical symptoms of viral infection include, but are not limited to high fever, severe aches and pains, headaches, and sore throat. MAAs for treating viral infections can be used or administered as a mixture, for example in equal amounts, or individually, provided in sequence, or administered all at once and can be administered orally, topically or parenterally in amounts sufficient to effect a reduction in the viral infection signs or symptoms. Further, the MAAs of the present invention can be co-administered with other well-known antigens, vaccines or adjuvants.

Likewise, active immunization for the prevention or protection against a viral infection involves administering one or more MAAs as a component of a vaccine. Vaccination can be performed orally, topically or parenterally in amounts sufficient to enable the recipient subject to generate protective immunity against the virus of interest to prevent the signs or symptoms of viral infection. An amount is said to be sufficient to prevent the signs or symptoms of viral infection if the dosage, route of administration, etc. of the MAA are sufficient to influence such a response. Responses to MAA administration can be measured by analysis of subject's vital signs or monitoring antibody titer.

An MAA composition suitable for administration is one which is tolerated by a recipient subject. Such MAA compositions can be prepared according to known methods of producing formulations, whereby the MAAs are combined in admixture with a pharmaceutically acceptable carrier. Pharmaceutically acceptable carriers are provided, for example, in Remington: The Science and Practice of Pharmacy, Alfonso R. Gennaro, editor, 20th ed. Lippingcott Williams & Wilkins: Philadelphia, Pa., 2000. In order to form an MAA composition suitable for administration, such compositions will contain an effective amount of the MAAs together with a suitable amount of a carrier, excipient, or stabilizer which is nontoxic to the cell or mammal being exposed thereto at the dosages and concentrations employed. In general, formulations will contain a final concentration of MAA in the range of 0.2 µg/mL to 2 mg/mL or more desirably 5 µg/mL to 500 µg/mL. Often the carrier is an aqueous pH buffered solution. Examples of pharmaceutically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

MAAs, or compositions or formulations containing an MAA of the invention can further contain adjuvants to enhance a subject's T cell response to the antigen. Examples of such adjuvants include, but are not limited to, aluminum salts; Incomplete Freund's adjuvant; threonyl and n-butyl derivatives of muramyl dipeptide; lipophilic derivatives of muramyl tripeptide; monophosphoryl lipid A; 3'-de-O-acetylated monophosphoryl lipid A; cholera toxin; phosphorothionated oligodeoxynucleotides with CpG motifs; and adjuvants such as those disclosed in U.S. Pat. No. 6,558,670.

Administration of MAAs, or compositions or formulations containing an MAA disclosed herein can be carried out by any suitable means, including parenteral injection (such as intraperitoneal, subcutaneous, or intramuscular injection), orally, or by topical application of the MAAs (typically carried in a pharmaceutical formulation) to an airway surface.

For injection, the carrier will typically be a liquid, such as sterile pyrogen-free water, pyrogen-free phosphate-buffered saline solution, bacteriostatic water, or Cremophor (BASF, Parsippany, N.J.). For other methods of administration, the carrier can be either solid or liquid.

Topical application of the MAAs to an airway surface can be carried out by intranasal administration (e.g., by use of dropper, swab, or inhaler which deposits a pharmaceutical formulation intranasally). Topical application of the MAAs to an airway surface can also be carried out by inhalation administration, such as by creating respirable particles of a pharmaceutical formulation (including both solid particles and liquid particles) containing the MAAs as an aerosol suspension, and then causing the subject to inhale the respirable particles. Methods and apparatus for administering respirable particles of pharmaceutical formulations are well-known, and any conventional technique may be employed.

Oral administration can be in the form of solutions, suspensions, tablets, pills, capsules, sustained release formulations or powders and contain 10% to 95% of active ingredient, preferably 25% to 70%. Capsules, tablets and pills for oral administration to a subject may be provided with an enteric coating comprising, for example, copolymers of methacrylic acid and methyl methacrylate, cellulose acetate, cellulose acetate phthalate or hydroxypropylmethyl cellulose.

A composition of the invention can be administered in a manner compatible with the dosage formulation, and in such amount as will be prophylactically and/or therapeutically effective. The quantity to be administered, which is generally in the range of 0.1 μg to 250 μg of MAA per dose, depends on the subject to be treated, capacity of the subject's immune system to synthesize antibodies, and the degree of protection desired. A preferable range is from about 0.5 μg to about 20 μg per dose.

A suitable dose size is about 0.5 mL. Accordingly, a dose for intramuscular injection, for example, would comprise 0.5 mL containing ~5 μg of MAA in admixture with 0.5% adjuvants.

The exact dosage will be determined by the skilled practitioner, in light of factors related to the subject that requires treatment. Dosage and administration are adjusted to provide sufficient levels of the active MAA or to maintain the desired effect of preventing or reducing viral signs or symptoms, or reducing severity of the viral infection. Factors which may be taken into account include the severity of the disease state, general health of the subject, age, weight, and gender of the subject, diet, time and frequency of administration, drug combination(s), reaction sensitivities, and tolerance/response to therapy.

The composition can be given in a single dose schedule, or desirably in a multiple dose schedule. A multiple dose schedule is one in which a primary course of administration may be with 1-10 separate doses, followed by other doses given at subsequent time intervals required to maintain and or reinforce the immune response, for example, at 1 to 4 months for a second dose, and if needed, a subsequent dose(s) after several months. The dosage regimen will also, at least in part, be determined by the need of the individual and be dependent upon the judgement of the practitioner.

The invention is described in greater detail by the following non-limiting examples.

EXAMPLE 1

Synthesis of Multiple Antigenic Agent Constructs (MAAs)

The solid-phase synthesis of exemplary MAA constructs of Formula I presented in Table 1 was carried out using a combination of three quasi-orthogonally removable amino protecting groups according to well-known methods (Kragol and Otvos (2001) *Tetrahedron* 57:957-66).

TABLE 1

| Valency of M2e | Construct | SEQ ID NO: |
|---|---|---|
| 1 | (1) M2e24-Man-MAA<br><br>    Man<br>    \|<br>    Ser<br>    \|<br>Lys-Gly-Lys-Gly-Lys-Gly-Lys-Gly-Lys-Gly-Lys-Gly-β-Ala<br> \|       \|       \|      \|      \|<br>Ser   Ser   Ser   S1   S2   M2e24<br> \|       \|       \|<br>Man  Man  Man | 2 |
|  | (1) M2e24-MAA<br><br>Lys-Gly-Lys-Gly-Lys-Gly-Lys-Gly-Lys-Gly-Lys-Gly-β-Ala<br>          \|     \|     \|    \|    \|<br>          Ser  Ser  S1  S2  M2e24 | 3 |
|  | (1) M2e24-MAP<br><br>    Ser<br>    \|<br>Lys-Gly-Lys-Gly-Lys-Gly-Lys-Gly-Lys-Gly-Lys-Gly-β-Ala<br> \|      \|     \|    \|    \|<br>Ser  Ser  Ser  S1  S2  M2e24 | 4 |
| 2 | (2) M2e24-MAA<br><br> Ser<br> \|<br>Cys-Gly-Lys-Gly-Lys-Gly-Lys-Gly-Lys-Gly-β-Ala<br>      \|     \|     \|     \|<br>    Ser  S2  S1  M2e24 M2e24 | 5 |
|  | (2) M2e24-MAP<br><br>Cys-Gly-Lys-Gly-Lys-Gly-Lys-Gly-Lys-Gly-β-Ala<br>      \|     \|    \|    \|<br>    S1  S2  M2e24 M2e24 | 6 |
| 4 | (4) M2e24-MAA<br><br>Cys-Gly-Lys-Gly-Lys-Gly-Lys-Gly-Lys-Gly-β-Ala<br> \|    \|    \|    \|    \|<br> S   S1  S2  M2e24 M2e24<br> \|<br> S<br> \|<br>Cys-Gly-Lys-Gly-Lys-Gly-Lys-Gly-Lys-Gly-β-Ala<br>      \|    \|    \|    \|<br>    S1  S2  M2e24 M2e24 | 7 |
|  | (4) M2e15-MAP<br><br>Lys-Gly-Lys-Gly-Lys-Gly-Lys-Gly-Lys-Gly-Lys-Gly-β-Ala<br> \|      \|     \|   \|     \|    \|<br>M2e15 M2e15 S1  S2  M2e15 M2e15 | 8 |

Man = mannose;
T cell determinant S1 = Ser-Phe-Glu-Arg-Phe-Glu-Ile-Phe-Pro-Lys-Glu (SEQ ID NO:9);
T cell determinant S2 = His-Asn-Thr-Asn-Gly-Val-Thr-Ala-Ala-Ser-Ser-His-Glu (SEQ ID NO:10);
B cell determinant M2e24 = Ser-Leu-Leu-Thr-Glu-Val-Glu-Thr-Pro-Ile-Arg-Asn-Glu-Trp-Gly-Cys-Arg-Ser-Asn-Asp-Ser-Ser-Asp-Pro (SEQ ID NO:11); and
B cell determinant M2e15 = Ser-Leu-Leu-Thr-Glu-Val-Glu-Thr-(Pro/His/Leu)-Ile-Arg-Asn-Glu-Trp-Gly (SEQ ID NO:12).
In the M2e15 construct, the residue in parenthesis is either proline, histidine or leucine.

The disulfide-linked octameric peptide construct (4)M2e24-MAA carrying four copies of M2e24 as well as two copies each of helper T cell determinants S1 and S2, was made via intermolecular disulfide formation from free sulfhydryl-bearing cysteine derivatives in solution (Kragol, et al. (2001) *Bioorg. Med. Chem. Lett.* 11:1417-20).

Peptide constructs for use as immunosorbents in ELISA to measure antibody titers against MAA backbone and M2e24 constructs respectively included the Cys-backbone construct consisting of:

Cys-Gly-Lys-Gly-Lys-Gly-Lys-β-Ala (SEQ ID NO:13), and the Cys-M2e24 construct consisting of:

Cys-Gly-Lys-Gly-Lys-Gly-Lys-β-Ala
           \|        \|
         M2e24  M2e24

(SEQ ID NO:14). These constructs were assembled on a continuous flow automated peptide synthesizer Miligen 9050 using conventional Fmoc chemistry (Fields and Noble (1990) *Int. J. Pept. Protein Res.* 35:161-214). Fmoc TENTAGEL™ S RAM resin (Advanced Chem Tech, Louisville, Ky.) with an initial load of 0.3 mmol/g was used. For chain elongation, a four molar excess of the amino acids was activated in situ with HATU. The coupling times ranged from 1 to 2.5 hours according to coupling difficulties predicted by the Peptide Companion algorithm (Windowchem, Fairfield, Calif.). During the synthesis of peptide construct Cys-backbone, the N-terminal amino group of Cys was protected with a Boc group while the Lys side chain amino group carried Aloc protection. The selective removal of the Aloc group by catalytic hydrogenation, followed by simultaneous peptide chain assembly of two M2e24 peptides gave the fully protected peptide construct Cys-M2e24. The peptides were cleaved from the resin by trifluoroacetic acid in the presence of 5% thioanisol and 5% water, and purified by RP— HPLC. The purity of the peptides was confirmed by RP-HPLC and MALDI mass spectrometry.

Peptide-DNA chimeras are prepared by one of two methods. On method involves co-synthesizing the peptidic or nucleic acid fragments using conventional Fmoc-chemistry and suitable hydroxy-carboxylic acid linkers (Soukchareun, et al. (1995) *Bioconjugate Chemistry* 6:43-53). A second method involves chemical ligation using thiol-containing bifunctional coupling reagents (Soukchareun, et al. (1998) *Bioconjugate Chemistry* 9:466-475; Stetsenko and Gait (2000) *J. Org. Chem.* 65:4900-4908).

EXAMPLE 2

Media and Solutions

ISC-CM consisted of Iscove's Dulbecco's medium (Life Technologies, Gaithersburg, Md.) supplemented with 2-mercaptoethanol at 0.05 mM, transferrin (Sigma, St. Louis, Mo.) at 0.005 mg/ml, glutamine (JRH Biosciences, Lenexa, Kans.) at 2 mM and gentamicin (Mediatech, Herndon, Va.) at 0.05 mg/ml. ISC-CM was further supplemented, as indicated, with fetal calf serum (FCS) (HyClone Laboratories, Logan, Utah) or bovine serum albumin (BSA) (Sigma, St. Louis, Mo.). Phosphate buffered saline, pH 7.2, was supplemented with 3 mM $NaN_3$ (PBSN).

EXAMPLE 3

Viruses

PR8 (A/PR/8/34(H1N1)) was a mouse-adapted strain. PR8-SEQ14 was an escape mutant selected from PR8 sequentially in the presence of 14 different PR8(HA)-specific monoclonal antibodies. X31 was a reassortant virus containing all PR8 derived genes except those coding for H3 and N2, which were from (A/Aichi/68(H3N$_2$)) (Kilbourne (1969) *Bull. WHO* 41:643-5). JAP was (A/Japan/305/57 (H2N$_2$)) and B/LEE was the type B influenza virus strain B/Lee/40.

EXAMPLE 4

Production of M2e24-Specific Hybridomas

Three M2e24-specific hybridomas (M2-56, M2-80, M2-86) were derived from a BALB/c mouse that had been challenged with two consecutive infections, the first with PR8 and the second with X31. Three days before fusion, the mouse was injected intravenously (i.v.) with 5 μg (4)M2e24-MAA in PBS and spleen cells fused with Sp2/O myeloma cells. Two hybridomas (M2-1, M2-15) were derived from a mouse that had recovered from three consecutive heterosubtypic infections (first with PR8, second with X31, third with JAP) and was boosted intranasally (i.n.) with 5 μg (4)M2e24-MAA together with 3 μg phosphorothionated oligodeoxynucleotide (ODN) c1826 and 0.5 μg cholera toxin (CT). Cells from draining lymphnodes (superficial cervical and mediastinal) were fused three days later. Hybrid cultures were screened for secretion of antibodies that reacted in ELISA with (1)M2e24-MAA and/or JAP-infected Madin Darby canine kidney (MDCK) cells. All M2e24-specific hybridomas generated by these protocols cross-reacted with M2e24-MAA and JAP-infected MDCK cells at roughly equimolar amounts, indicating that the M2e-MAAs shared several B cell determinants in common with native M2e. The hybridoma 14C2 is well-known in the art (Zebedee and Lamb (1988) supra).

EXAMPLE 5

Antibody Measurements by ELISA

Wells of Costar serocluster, round-bottom, polyvinyl plates were coated with (1)M2e24-MAA by incubation overnight at room temperature (covered to prevent evaporation) with 25 μL of the construct at 0.5 μg/mL in PBSN. The plates were blocked for one to two hours with PBSN containing 1% BSA prior to assay. JAP-MDCK ELISA plates were prepared as follows: MDCK cells were grown to confluency in FALCON®, microtest, flat-bottom, 96-well, polystyrene, tc plates, typically by seeding wells with 4×10$^4$ MDCK cells in 100 μL of ISC-CM containing 5% FCS. After one day of incubation (37° C., 6% CO$_2$), monolayers were washed with PBS to remove serum components and infected by incubation (37° C.) with 50 μL of ISC-CM containing ~106 TCID$_{50}$ of JAP virus. After one hour, 100 μL of ISC-CM containing 5% FCS was added to each well and incubation continued as above for six to seven hours. Monolayers were then washed with PBS, fixed by incubation for five minutes at room temperature with 5% buffered FORMALDE-FRESH® (FisherChemical, Pittsburgh, Pa.), washed with PBSN and blocked and stored with PBSN containing 1% BSA at 4° C. In ELISA, all test samples and reagents were diluted in PBSN containing 1% BSA, used at 25 μL/round-bottom well or 50 μL/flat-bottom well, and incubated for 90 minutes at room temperature. Bound mouse antibody was generally detected with biotinylated rat-anti-mouse-Cκ monoclonal antibody 187.1, followed by Streptavidin-AP (Sigma, St. Louis, Mo.) and pNPP (Sigma, St. Louis, Mo.). The pNPP solution was used at 50 μL and 100 μL per round- and flat-bottom well, respectively. Absorption was measured with the EMAX® plate reader (Molecular Devices, Sunnyvale, Calif.) and the difference between OD$_{405}$ and OD$_{750}$ (OD$_{405-750}$) recorded, usually after 30-45 minute of incubation. All assays included a titration of a purified monoclonal antibody of appropriate specificity for quantification of test samples. ELISA data were analyzed with the SOFTMAX PRO® software (Molecular Devices, Sunnyvale, Calif.).

The structurally different M2e24-MAAs showed no significant differences in reactivity with M2e-specific monoclonal antibodies in ELISA. All monoclonal antibodies reacted equally well with equimolar amounts of the MAA containing (4)M2e24-MAA and (4)M2e15-MAP having a proline at position 10, indicating that the relevant B cell determinant shared by native and synthetic M2e is formed by the N-terminal region of M2e.

EXAMPLE 6

Analysis of CD4$^+$ T Cell Responses

Antigen presenting cells (APC) were prepared from the spleen of naïve BALB/c mice. PERCOLL™ (PHARMACIA®, Uppsala, Sweden) was added to the cell suspension to give a final concentration of 33%. The suspension was underlayed with a small volume of 70% PERCOLL™ and centrifuged (10 minutes, 600 grams, room temperature) to remove cell debris and erythrocytes. Cells at the 33%/70% interface were harvested, washed, irradiated (2200 rad) and suspended in ISC-CM at 5×10$^6$ cells/mL. One hundred μL were dispensed per well of flat-bottomed tissue culture plates. Antigen in ISC-CM was added in 50 μL volumes per well. Fifty μL of responder cell suspension, typically MedLN cells at 10$^7$/mL or Th clones at 4×10$^5$/mL in ISC-CM, were added per well. One μCi of H$^3$-thymidine was added during the third (Th clones) or fourth (LN responder cells) day of incubation. Plates were then frozen and thawed once and the cells were harvested with a Skatron cell harvester (Skatron Instruments Inc., Sterling, Va.) onto filter mats (Skatron Instruments Inc., Sterling, Va.). Punched out pieces of filter mat were transferred into scintillation fluid and counted for radioactivity.

On a molar basis, M2e24-MAAs exhibited similar potency as free S1 peptide in stimulating S1-specific Th cells with one notable exception: the mannosylated MAP ((1)M2e24-Man-MAA) exhibited a 100- to 1000-fold higher stimulatory potency in vitro than free S1 peptide and non-mannosylated MAAs. The stimulatory potency was comparable to purified intact HA which contains the S1 determinant in the context of the intact HA1 polypeptide and also contains mannosylated carbohydrate side chains.

EXAMPLE 7

Analysis of CD8$^+$ Memory T Cell Response

Spleen cells from vaccinated mice were purified as provided in a 33%/70% PERCOLL™ gradient and used as responder cells. A20 cells (H2$^d$, positive for MHC class II) were infected with PR8 (106 TCID$_{50}$/10$^6$ A20, one hour at 37° C.), irradiated with 4400 rad, washed and used as stimulators. Cultures (6 mL) were set up in T25 FALCON® flasks and contained 25×10$^6$ responder cells and 10$^6$ stimulator cells in ISC-CM containing 5% FCS. After five days of incubation (stationary, upright), viable cells were purified in a 33%/70% PERCOLL™ gradient, counted and using standard methods (Mozdzanowska, et al. (1997) *Virology* 239: 217-25) tested for the ability to induce release of $^{51}$Cr from PR8- and B/LEE-infected P1.HTR target cells during a four-hour incubation period.

EXAMPLE 8

Immunization Protocols

M2e-MAAs and adjuvants, in a total volume of 50 μL, were placed onto the nares of anesthetized mice (ketamine and xylazine injected intraperitoneally at 70 mg/kg and 7 mg/kg body weight, respectively), which resulted in its aspiration into the respiratory tract. One dose of 50 μL contained 3 μg of M2e-MAA, 3 μg of the ODN 1826 (Krieg, et al. (1995) *Nature* 374:546-9; Yi, et al. (1998) *J. Immunol.* 160:4755-61) and 0.5 μg of CT (Sigma, St. Louis, Mo.). Adjuvant combination and dosing was based on standard methods (Mozdzanowska, et al. (1999) supra). Booster inoculations were administered in four to five week intervals. Mice that received adjuvant solution without M2e-MAA were used as negative controls and mice that had been subjected to two consecutive respiratory tract infections, first with PR8 and second with PR8-SEQ 14, were used as positive controls.

EXAMPLE 9

Virus Challenge Experiments

The strength of vaccine-induced protection was tested by i.n. challenge of mice with ~$10^3$ MID$_{50}$ (50% mouse infectious dose) of X31. Three days later, the mice were anesthetized, exsanguinated by heart puncture, and dissected for collection of nasal, tracheal and pulmonary tissues. Titers of infectious virus were determined by titration of tissue homogenates in MDCK cell cultures or embryonated hen's eggs using standard methodologies (McCluskie and Davis (2000) supra).

EXAMPLE 10

In Vitro Analysis of Immune Response to MAAs

To induce a Th-dependent antibody response to native viral M2e, M2e-MAAs shared B cell epitopes with native virus-induced M2e and contained determinants that could be presented to Th cells. JAP-MDCK cells and M2e-MAAs were compared for their reaction with several M2e-specific monoclonal antibodies in ELISA. The 14C2 monoclonal antibody was generated from a mouse immunized with purified viral M2 (Zebedee and Lamb (1988) supra); all other antibodies were isolated from mice recovered from consecutive influenza type A virus infections and boosted with (4)M2e24-MAA three days prior to fusion. The final boost with (4)M2e24-MAA was performed to increase the frequency of isolation of M2e-specific hybridomas. All six M2e-specific monoclonal antibodies reacted well with both M2e-MAA and JAP-MDCK, though four were slightly more and two slightly less effective in binding to JAP-MDCK than to wells coated with (1)M2e24-MAA at 1.5 ng/well. The data indicated that M2e-MAAs mimicked effectively several B cell determinants of the native virus-induced tetrameric M2e.

The structurally different M2e-MAAs, when used at equimolar M2e concentrations, showed no significant differences in reaction with M2e-specific monoclonal antibodies.

To optimize Th-mediated help, two distinct Th determinants were incorporated into the MAAs, one (S1) presented by $E^d$ and the other (S2) by $A^d$. These determinants were identified as the two immunodominant targets of the HA(PR8)-specific Th response of BALB/c (H-$2^d$) mice (Gerhard, et al. (1991) *J. Virol.* 65:364-72). S1 corresponds to the HA region 110-120 and S2 to 126-138. However, the S2 peptide in the present constructs was altered compared to the native S2 by replacing the cysteine at position 135 with serine to avoid formation of disulfide bonds between S2 and the cysteine contained in the M2e peptide.

The efficacy of the MAAs to stimulate S1- and S2-specific Th clones was determined in cultures that contained irradiated BALB/c spleen cells as APCs, S1- or S2-specific Th clones as responders and various concentrations of free S1 or S2 peptides, M2e-MAAs or purified HA. Proliferation of the Th clones was assessed by $^3$H-thymidine incorporation during the third day of culture. All M2e-MAAs stimulated the S1-specific Th clone V2.1 with equal or higher potency than the free S1 peptide. A 100-fold greater stimulatory potency of the mannosylated MAA was observed most likely due to improved capture of this MAA by mannose-receptors expressed on APCs (Engering, et al. (1997) *Eur. J. Immunol.* 27:2417-2; Tan, et al. (1997) *Eur. J. Immunol.* 27:2426-35). The stimulatory activity of this MAA is similar, on a molar basis, to the activity of the HA molecule which also contains mannosylated carbohydrate side chains (Keil, et al. (1985) *EMBO J.* 4:2711-20).

By contrast, none of the MAAs stimulated the S2-specific Th clone 5.1-5R6. This Th clone responded well to stimulation with the isolated native S2 peptide and intact HA, thus the change of Cys(135) to Ser may have reduced its stimulatory potency for this Th clone. Two additional, clonally unrelated, S2-specific Th clones were tested and also failed to respond to MAAs. Since the Cys(135)→Ser does not to affect the peptide's ability to bind to $A^d$ (Sette, et al. (1989) *J. Immunol.* 142:35-40), it may form an antigenically novel Th determinant which is not recognized by Th specific for the native S2 determinant. Crystal structure analysis of the S2/Ad complex indicated that the amino acid at position 135 is not an anchor residue (Scott, et al. (1998) *Immunity* 8:319-29).

Thus, the in vitro analyses indicated that the M2e-MAAs mimicked B cell determinants of the native virus-induced M2e and contained at least one functional Th determinant.

What is claimed is:

1. A multiple antigenic agent comprising:

wherein, $R_1$ is 0 to 2 amino acid residues comprising Cys or Gly, or a nucleic acid sequence; n is at least 1; $Xaa_1$ is 0 to 1 amino acid residue comprising or Gly; $R_3$ is a B cell determinant; $R_4$ is a targeting molecule; and $R_5$ is any amino acid.

2. A composition comprising the multiple antigenic agent of claim 1 and a pharmaceutically acceptable carrier.

3. The composition of claim 2, wherein the composition further comprises an adjuvant.

4. The composition of claim 2, wherein the composition comprises a vaccine.

5. The composition of claim 3, wherein the composition comprises a vaccine.

* * * * *